(12) United States Patent
Clement et al.

(10) Patent No.: US 9,662,308 B2
(45) Date of Patent: May 30, 2017

(54) ORALLY BIOAVAILABLE PENTAMIDINE PRODRUGS FOR THE TREATMENT OF DISEASES

(71) Applicant: Dritte Patentportfolio Beteiligungsgesellschaft mbH & Co. KG, Schoenefeld/Waltersdorf (DE)

(72) Inventors: Bernd Clement, Kiel (DE); Joscha Kotthaus, Kiel (DE); Jürke Kotthaus, Kiel (DE); Dennis Schade, La Jolla, CA (US)

(73) Assignee: Dritte Patentportfolio Beteiligungsgesellschaft mbH & Co. KG, Schönefeld, Waltersdorf (DE)

( * ) Notice: Subject to any disclaimer, the term of this patent is extended or adjusted under 35 U.S.C. 154(b) by 360 days.

(21) Appl. No.: 14/581,384

(22) Filed: Dec. 23, 2014

(65) Prior Publication Data
US 2015/0111965 A1    Apr. 23, 2015

Related U.S. Application Data

(60) Continuation-in-part of application No. 14/455,272, filed on Aug. 8, 2014, now Pat. No. 9,353,047, which
(Continued)

(30) Foreign Application Priority Data

Feb. 1, 2008  (DE) .................. 10 2008 007 381
Jul. 25, 2011  (EP) ..................... 11175252

(51) Int. Cl.
C07C 259/18    (2006.01)
A61K 31/225    (2006.01)
(Continued)

(52) U.S. Cl.
CPC .......... *A61K 31/225* (2013.01); *A61K 31/138* (2013.01); *A61K 31/366* (2013.01);
(Continued)

(58) Field of Classification Search
None
See application file for complete search history.

(56) References Cited

U.S. PATENT DOCUMENTS 5,786,383 A    7/1998  Clement
7,115,665 B1   10/2006  Chow et al.
(Continued)

FOREIGN PATENT DOCUMENTS

CA    2572161 A1    1/2006
DE    43 21 444 A1  1/1995
(Continued)

OTHER PUBLICATIONS

EP Search Report issued Oct. 18, 2011 in EP Application No. 11175252.3.
(Continued)

*Primary Examiner* — Sudhakar Katakam
*Assistant Examiner* — Jennifer C Sawyer
(74) *Attorney, Agent, or Firm* — Panitch Schwarze Belisario & Nadel LLP

(57) ABSTRACT

The present invention relates to prodrug derivatives of pentamidine, their use in the treatment and/or prophylaxis of diseases such as tumor diseases, as well as leishmaniasis, trypanosomiasis, pneumocystis carinii pneumonia (PcP), and malaria.

11 Claims, 6 Drawing Sheets

Related U.S. Application Data is a division of application No. 12/847,415, filed on Jul. 30, 2010, now abandoned, which is a continuation of application No. PCT/EP2009/051132, filed on Feb. 2, 2009, application No. 14/581,384, which is a continuation of application No. 13/554,536, filed on Jul. 20, 2012, now abandoned.

(51) Int. Cl.
| | |
|---|---|
| A61K 31/436 | (2006.01) |
| A61K 31/138 | (2006.01) |
| A61K 31/366 | (2006.01) |
| A61K 31/4196 | (2006.01) |
| A61K 31/506 | (2006.01) |
| A61K 31/517 | (2006.01) |

(52) U.S. Cl.
CPC ........ *A61K 31/4196* (2013.01); *A61K 31/436* (2013.01); *A61K 31/506* (2013.01); *A61K 31/517* (2013.01); *C07C 259/18* (2013.01)

(56) References Cited

U.S. PATENT DOCUMENTS

| | | | |
|---|---|---|---|
| 7,608,623 B2 | 10/2009 | Sperl et al. | |
| 2008/0319016 A1* | 12/2008 | Hayashi | C07D 211/22 514/317 |
| 2009/0136980 A1 | 5/2009 | Bebbington et al. | |
| 2009/0270440 A1 | 10/2009 | Clement et al. | |
| 2011/0028756 A1 | 2/2011 | Clement et al. | |
| 2012/0128667 A1 | 5/2012 | Chow et al. | |

FOREIGN PATENT DOCUMENTS

| | | |
|---|---|---|
| DE | 103 23 898 A1 | 12/2004 |
| DE | 10 2006 034 256 A1 | 1/2008 |
| EP | 1767526 A1 | 3/2007 |
| JP | 2001-031586 A | 2/2001 |
| JP | 2004-510703 A | 4/2004 |
| JP | 2004-537527 A | 12/2004 |
| JP | 2005-509606 A | 4/2005 |
| WO | 0195945 A2 | 12/2001 |
| WO | 03028729 A2 | 4/2003 |
| WO | 2005049636 A2 | 6/2005 |
| WO | 2008/009264 A1 | 1/2008 |

OTHER PUBLICATIONS

Kotthaus et al., Synthesis and biological evaluation of L-valine-amidoximeesters as double prodrugs of amidines, Bioorganic & Medicinal Chemistry, vol. 19, pp. 1907-1914, (2011).
Chow et al, "The DNA double-stranded break repair protein endo-exonuclease as a therapeutic target for cancer", Molecular Cancer Therapeutics, vol. 3, No. 8, pp. 911-919 (2004).
Clement, "Reduction of N-Hydroxylated Compounds: Amidoximes (N-Hydroxyamidines) as Pro-Drugs of Amidines", Drug Metabolism Reviews, vol. 34, No. 3, pp. 565-579 (2002).
Clement et al, "Enzymatic Reduction of Benzamidoxime to Benzamidine", Arch. Pharm. (Weinheim), vol. 321, pp. 955-956 (1988).
Clement et al, "Reduction of Amidoxime Derivatives to Pentamidine in vivo", Arch. Pharm. (Weinheim), vol. 325, pp. 61-62 (1992).
Havemeyer et al, "Identification of the Missing Component in the Mitochondrial Benzamidoxime Prodrug-converting System as a Novel Molybdenum Enzyme", Journal of Biological Chemistry, vol. 281, No. 46, pp. 34796-34802 (2006).
Gruenewald et al, "The Fourth Molybdenum Containing Enzyme mARC: Cloning and Involvement in the Activation of N-Hydroxylated Prodrugs", Journal of Medicinal Chemistry, vol. 51, pp. 8173-8177 (2008).
Clement et al, "Diacetyldiamidoximeester of Pentamidine, a Prodrug for Treatment of Protozoal Diseases: Synthesis, in vitro and in vivo Biotransformation", ChemMedChem, vol. 1, pp. 1260-1267 (2006).
Arafa et al, "Synthesis, DNA Affinity, and Antiprotozoal Activity of Fused Ring Dicationic Compounds and Their Prodrugs", Journal of Medicinal Chemistry, vol. 48, pp. 5480-5488 (2005).
Brendle et al, "Antileishmanial Activities of Several Classes of Aromatic Dications", Antimicrobial Agents and Chemotherapy, vol. 46, No. 3, pp. 797-807 (2002).
Donkor et al, "Trypanocidal Activity of Conformationally Restricted Pentamidine Congeners", Journal of Medicinal Chemistry, vol. 46, pp. 1041-1048 (2003).
Ismail et al, "Dicationic biphenyl benzimidazole derivatives as antiprotozoal agents", Bioorganic & Medicinal Chemistry, vol. 12, pp. 5405-5413 (2004).
Int'l Preliminary Report on Patentability issued Feb. 6, 2014 in Int'l Application No. PCT/EP2012/064171.
Int'l Search Report issued on May 20, 2009 in Int'l Application No. PCT/EP2009/051132.
Written Opinion issued on May 20, 2009 in Int'l Application No. PCT/EP2009/051132.
English Translation of Response to Written Opinion on Dec. 28, 2009 in Int'l Application No. PCT/EP2009/051162.
Reeh et al., "N, N'-Dihydroxyamidines: A New Prodrug Principle to Improve the Oral Bioavailability of Amidines," Journal of Medicinal Chemistry, vol. 50, No. 26, pp. 6730-6734, (2007).
Sridhar Varadarajan: "ProDrugs", [Internet Article], pp. 1-5; URL: http://uncw.edu/chem/courses/varadarajan/chm417//Course %20Materials/Prodrugs.pdf, [Retrieved on Apr. 19, 2007].
Int'l Preliminary Report on Patentability issued on Apr. 16, 2010 in Int'l Application No. PCT/EP2009/051132.
Office Action Issued Sep. 29, 2008 in German Appln. Ser. No. 10 2008 007 381.4.
Office Action issued Dec. 6, 2012 in AU Application No. 2009209560.
German translation of an Office Action issued Aug. 5, 2013 in JP Application No. 2010-544724.
Wolff, Manfred E. "Burger's Medicinal Chemistry, 5ed, Part 1", John Wiley & Sons, 1995, pp. 975-977.
Banker, G.S. et al, "Modern Pharmaceutics, 3ed.", Marcel Dekker, New York, 1996, p. 596.
Tao et al. (Bioorg. Med. Chem. Let., 1999, 9, 1299).
Huang et al. (J. Pharmacy and Pharmacology, 2006, 58, 1033).
DrugBank pentamidine description (http://www.drugbank.ca/drugs/DB00738), 2011.
Office Action issued Nov. 17, 2011 in U.S. Appl. No. 12/847,415.
Office Action issued Mar. 27, 2012 in U.S. Appl. No. 12/847,415.
Office Action issued Aug. 22, 2013 in U.S. Appl. No. 12/847,415.
Office Action issued Apr. 8, 2014 in U.S. Appl. No. 12/847,415.
English translation of an Office Action issued Jun. 4, 2014 in CN Application No. 200980103401.7.
Search Report issued Mar. 27, 2014 in EP Application No. 14155230.7.
English translation of an Office Action issued Apr. 27, 2014 in IL Application No. 207286.
Office Action issued Nov. 13, 2014 in CA Application No. 2,713,784.

* cited by examiner

ORALLY BIOAVAILABLE PENTAMIDINE PRODRUGS FOR THE TREATMENT OF DISEASES

CROSS-REFERENCE TO RELATED APPLICATIONS

This application is a Continuation of U.S. application Ser. No. 13/554,536 filed Jul. 20, 2012, published as US Patent Application Publication No. 20130085180 on Apr. 4, 2013, which claims priority to European Patent Application No. 11175252.3, filed Jul. 25, 2011. This application is also a Continuation-in-Part patent application of U.S. application Ser. No. 14/455,272 filed Aug. 8, 2014, published as US Patent Application Publication No. US20140350293 on Nov. 27, 2014, which is a Division of U.S. application Ser. No. 12/847,415 (now abandoned), published as US Patent Application Publication No. 20110028756 on Feb. 3, 2011, which is a Continuation of PCT/EP2009/051132 filed Feb. 2, 2009, claiming priority to German Patent Application No. 10 2008 007 381.4 filed on Feb. 1, 2008. The entire disclosure of each of the above referenced applications is incorporated herein by reference.

BACKGROUND OF THE INVENTION

The present invention relates to prodrug derivatives of pentamidine, their use for the treatment and/or prophylaxis of diseases, in particular tumor and cancer diseases, as well as leishmaniasis, trypanosomiasis, pneumocystis carinii pneumonia (PcP), as well as malaria. Pentamidine is an antiparasitically and antimicrobially active compound the use of which is established in the treatment of trypanosomiasis, leishmaniasis, as well as pneumocystis carinii pneumonia (PcP). Due to the two strongly basic amidine functions, the compound is charged under physiological conditions and will not be absorbed by the organism after oral application. This is the reason why the compound needs to be administered parenterally, e.g. by intramuscular, intravenous or inhalation routes. It must be borne in mind in this context that most of the infections caused by the pathogens mentioned above occur in tropical and subtropical countries where medical care is often insufficient. Complicated application forms as represented by intravenous and inhalation applications hence make safe drug therapy particularly difficult in these countries. For this reason, the developing of an orally bioavailable pentamidine prodrug is of enormous importance in order to improve the treatment options decisively. A further negative aspect is the non existing ability of pentamidine to pass into the CNS resulting in pentamidine being only effective in the early stage of trypanosomiasis (African sleeping sickness) rather than in the meningo-encephalitic phase in which pathogens penetrate into the CNS.

A further possible field of pentamidine application is cancer therapy. The inhibiting action of pentamidine to endo-exonuclease has been studied thoroughly during the past years.[1, 2] First clinical studies already showed promising results in the treatment of breast and colon carcinoma.[3] Here as well, the use of an orally bioavailable pentamidine prodrug is of great importance.

For these reasons, numerous tests have been conducted in order to improve both bioavailability and CNS passage. In previous studies, pentamidine was transferred into the pentamidine diamidoxime of lower basicity leading to a strong increase of lipophilicity. Since amidoximes are uncharged under physiological conditions, the absorption of these compounds from the gastrointestinal tract is drastically increased.[4] The marked reduction of the amidoximes into the pharmacologically active amidines could be shown for the first time in the year 1988 based on the model compound benzamidoxime.[5] The principle was transferred later to the pentamidine, whereby the pentamidine-monoamidoxime and pentamidine-diamidoxime (3) were obtained. In animal studies, both compounds showed low bioavailability and good ability to be activated into the active form pentamidine.[6] The enzyme system responsible for the reduction could in the meantime be identified as a hitherto unknown molybdenum-containing system which was called mARC (mitochondrial Amidoxime Reducing Component).[7, 8]

To optimize both the pharmacokinetic profile for improving bioavailability and the ability to pass into the CNS, further prodrugs have been developed. With the N,N-bis(acetoxy)pentamidine, a compound was obtained which has a clearly increased lipophilicity as compared to other pentamidine prodrugs. This prodrug as well could demonstrate oral bioavailability in animal studies on rats as well as pigs. A disadvantage of the N,N-bis(acetoxy)pentamidine is very low water solubility, on the one hand, the ascertained bioavailability, on the other, was very low and passage into the CNS, could not be confirmed.[9] Similar approaches led to the development of the N,N'-bis(methoxy)pentamidine which, similar to the N,N'-bis(acetoxy)pentamidine, had very low water solubility. Further prodrug principles which were transferred to pentamidine are the hydroxylating into the N,N'-bis(dihydroxy)pentamidine and the conjugation with amino acids (especially valine) into N,N'-bis(valoxy)pentamidine.[10-12] It must be stated in summary that a pentamidine prodrug could not be developed to date which meets the required criteria (good oral bioavailability, passage into the CNS, and good solubility) in an optimum manner.

BRIEF SUMMARY OF THE INVENTION

In the light of the above, the present invention was based on the task of providing pentamidine prodrugs which exhibit improved properties as compared to the known prodrugs of pentamidine.

The cited task is solved according to the invention by a compound of formula (I)

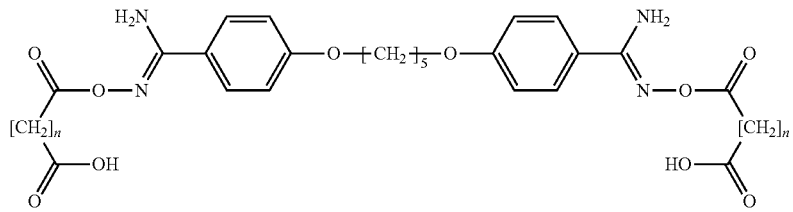

in which n represents 1 to 10, as well as pharmaceutically acceptable derivatives thereof.

In a preferred embodiment, n represents 2 in Formula (I).

In a further preferred embodiment, n represents 3 in Formula (I). In a further preferred embodiment, n represents 1, 3, 4, 5, 6, 7, 8, 9 or 10 in Formula (I).

Especially, N,N'-bis(succinyloxy)pentamidine (1) is clearly superior to the hitherto described pentamidine prodrugs. A considerable improvement of solubility was particularly stated which represents a very critical parameter of other pentamidine prodrugs. Due to this improved solubility, the pharmacokinetic behavior of the substance is positively influenced since good solubility properties constitute an important parameter in the absorbing of medicinal substances.

The present invention furthermore also relates to salts, solvates and solvates of the salts of the cited formula (I) compounds.

The present invention furthermore relates to the cited formula (I) compounds for the treatment and/or prophylaxis of diseases.

In a preferred embodiment, the present invention relates to the cited compounds for use in the treatment and/or prophylaxis of oncological diseases and tumor diseases of any pathogenesis.

In a further preferred embodiment, the present invention relates to the cited compounds for use in the treatment and/or prophylaxis of leishmaniasis, trypanosomiasis and/or pneumocystis carinii pneumonia (PcP).

In a further preferred embodiment, the present invention relates to the cited compounds for use in the treatment and/or prophylaxis of malaria.

The present invention furthermore relates to a drug comprising at least one of the cited formula (I) compounds, if appropriate in combination with one or more of inert, non-toxic, pharmaceutically suited excipients.

The present invention moreover also relates to a drug comprising at least one of the cited formula (I) compounds in combination with one or more further active agent(s).

The present invention moreover also relates to a drug for oral or parenteral application.

The present invention furthermore relates to a drug for the treatment and/or prophylaxis of oncological diseases and tumor diseases.

The present invention also further relates to a drug as described above which is of enteric formulation.

The present invention furthermore relates to a method for the treatment and/or prophylaxis of tumor diseases in humans or animals using at least one of the cited formula (I) compounds or one of the cited drugs.

Further, the present invention relates to a method for the treatment and/or prophylaxis of leishmaniasis, trypanosomiasis and pneumocystis carinii pneumonia (PcP).

The present invention also relates to a method for preparing a compound such as described above, in which the amidoxime of formula (A)

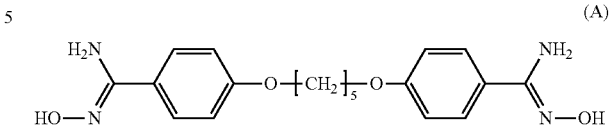

is converted by reacting with a dicarboxylic acid anhydride of formula (B)

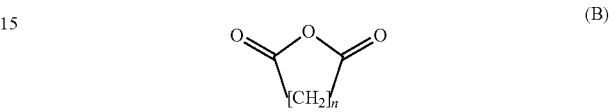

in which n represents 1 to 10,
into a compound of formula (C)

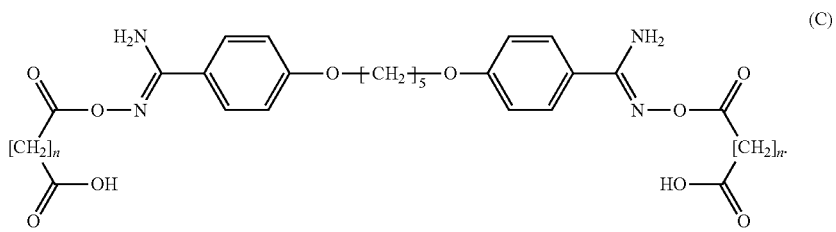

A further developed prodrug principle is the coupling of amidoximes to dicarboxylic acids such as described in the patent applications WO2009095499 and DE102008007381.11 Corresponding pentamidine prodrugs were developed with reference to these studies. The obtained compounds were characterized in detail and examined with respect to their bioavailability. Our studies showed that the pentamidine dicarboxylic acid derivatives are particularly suited pentamidine prodrugs which apart from excellent solubility also possess good oral bioavailability after oral application. Comparative analyses using other pentamidine prodrugs showed in this case the superiority of N,N'-bis(succinyloxy)pentamidine (1) to the hitherto described pentamidine prodrugs.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating, the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

The therapeutic use of pentamidine is hitherto very limited due to insufficient oral bioavailability. Particularly in the structurally weak Third World countries the development of an orally bioavailable medicinal substance constitutes a considerable progress in pharmacotherapy since it allows complicated and risky intravenous applications to be avoided. In addition are today's treatment options particularly in trypanosome, pneumocystis carinii, pneumocystis jirovecii and leihmania infections not satisfactory. For this reason, the main focus of this invention is the developing of an orally bioavailable prodrug of pentamidine.

In addition, an orally applicable pentamidine prodrug could gain considerable importance in cancer therapy. Pentamidine is presently examined in clinical studies against various kinds of cancer (breast and colon carcinoma). First clinical studies already showed promising results.[3] Here, as well, the novel pentamidine prodrugs could find application and improve therapy, even in combination with other oncological active agents.

Novel pentamidine prodrugs were developed within the framework of the present invention by linking the pentamidine diamidoxime (3) to dicarboxylic acids. The obtained compounds were comprehensively characterized in vitro and in vivo, wherein they showed excellent solubility as well as good bioavailability. Comparative analyses using different pentamidine prodrugs moreover showed the superiority of the newly developed N,N'-bis(succinyloxy)pentamidine (1) to pentamidine prodrugs described thus far.

Synthesis

Figure 1:
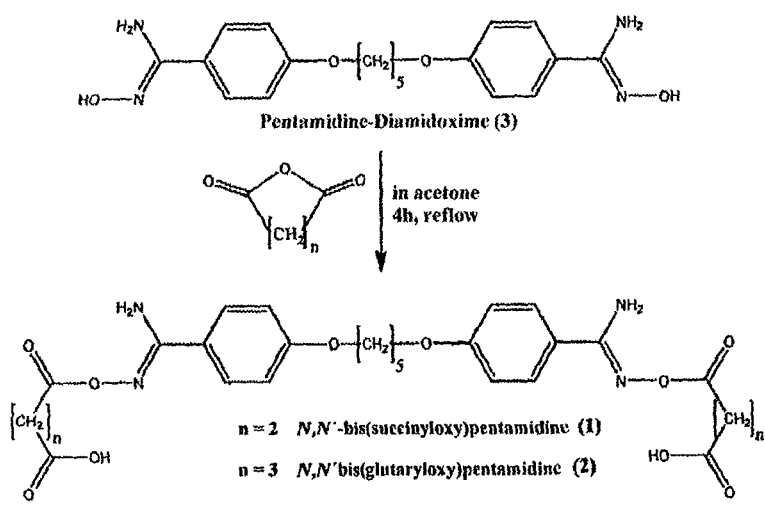
FIG. 1 is a schematic view of the synthesis of the pentamidine prodrugs.

The preparing of the prodrugs (1, 2) ensued from pentamidine diamidoxime (3) and the respective acid anhydride (succinic acid respectively glutaric acid anhydride). The starting compound was heated under reflux for 4 hours in dried acetone by adding succinic acid anhydride (see FIG. 1). The subsequent boiling up in toluene and direct filtering off allowed the substances 1 and 2 to be separated and the desired compounds to be prepared in an analytically pure form.

Stability

Figure 2:
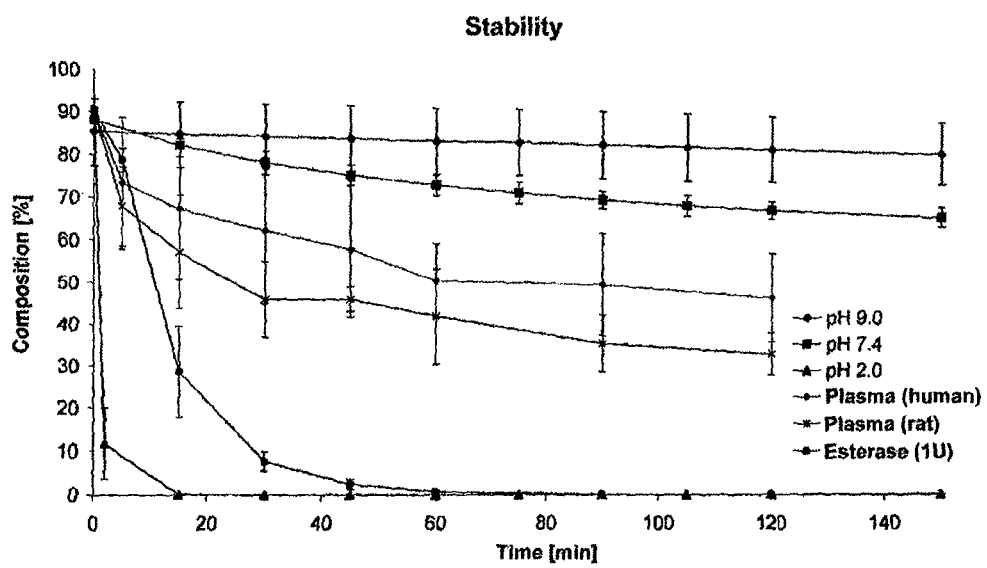
FIG. 2 is a stability of N,N'-bis(succinyloxy)pentamidine (1) at various pH values and in murine respectively human plasma, as well as at incubation with esterase.
Figure 3A:
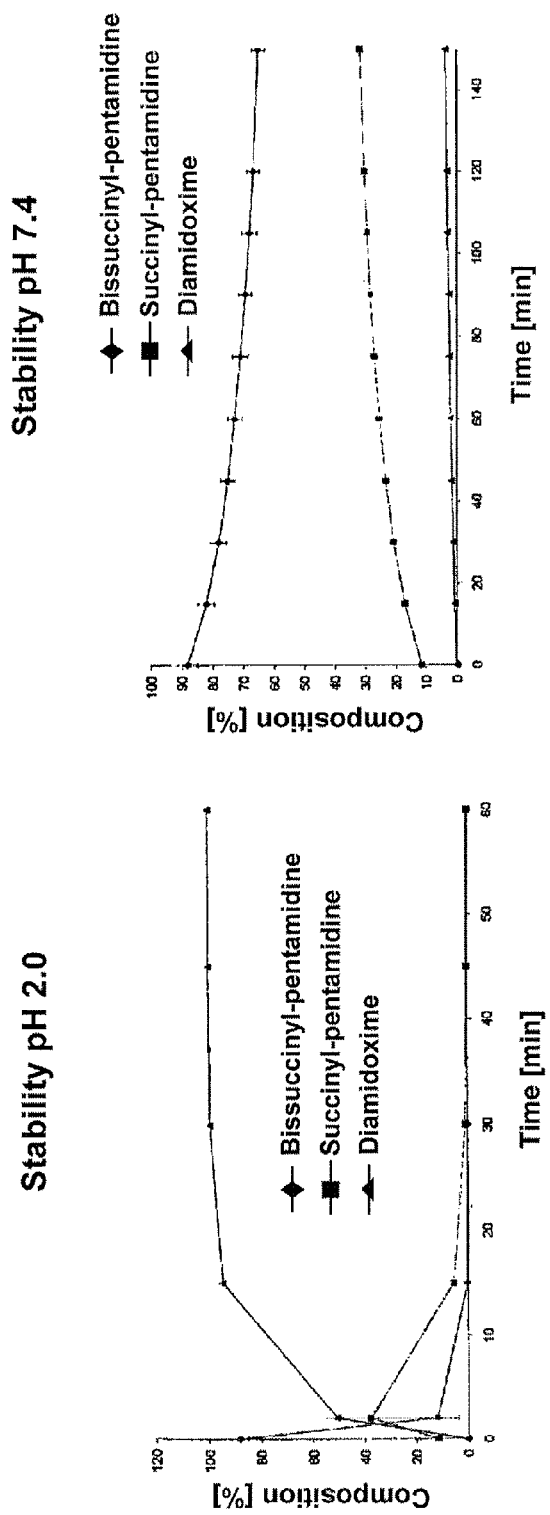
FIGS. 3A-3C are all a stability of N,N'-bis(succinyloxy) pentamidine (1) at various pH values and in murine respectively human plasma.
Figure 3B:
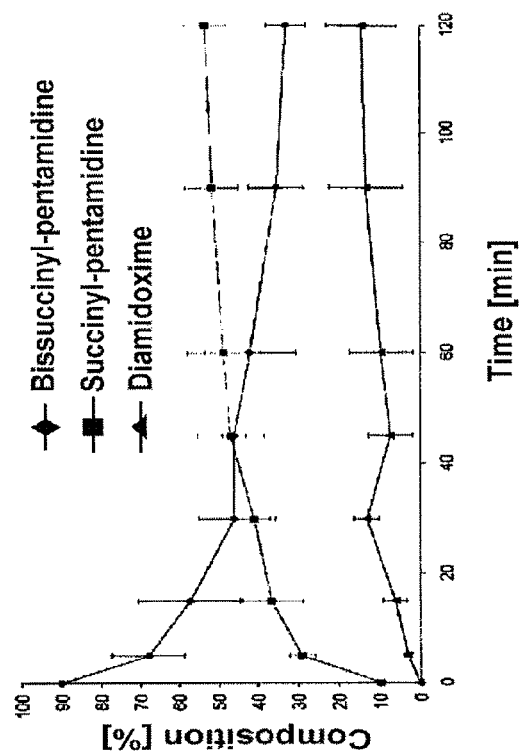
Figure 3B:
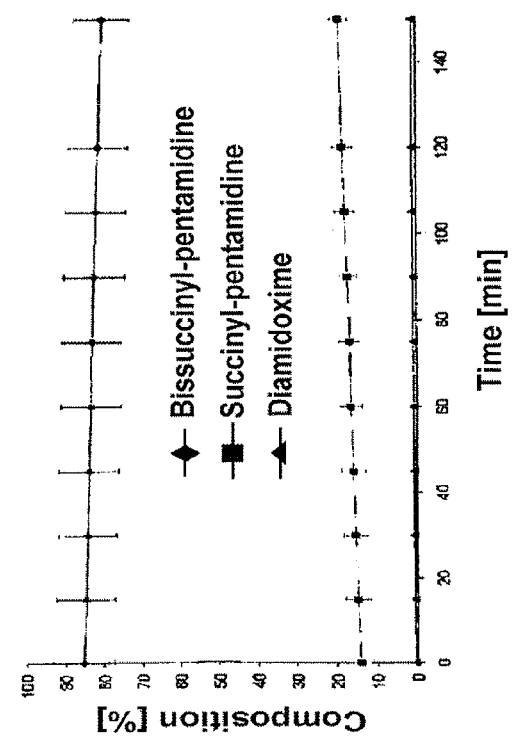
Figure 3C:
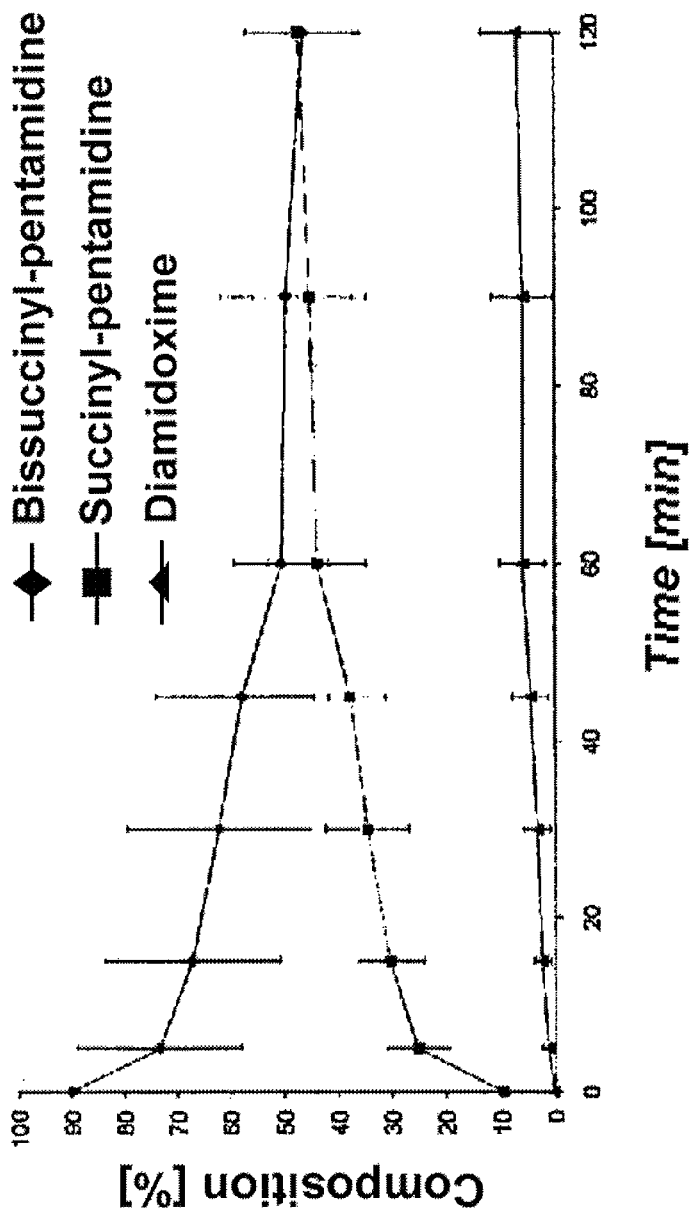

The analyses showed that compound 1 is stable in the neutral and slightly alkaline pH range, hence from pH 7.4 to pH 9.9. In acidic medium at pH 2.0, the compounds are rapidly hydrolytically cleaved (FIGS. 2, 3).

It showed during the analyses that the N,N'-bis(succinyloxy)pentamidine (1) hydrolized in aqueous medium into monosuccinyl pentamidine and pentamidine diamidoxime (3). While this hydrolysis proceeds at pH 7.4 and pH 9.0 only to a minor extent, it proceeds markedly at pH 2.0 in human as well as murine plasma. The rapid hydrolysis of the N,N'-bis(succinyloxy)pentamidine (1) at pH 2.0 (see FIGS. 2, 3) must be classified as being problematic with respect to the use as a prodrug. The N,N'-bis(succinyloxy)pentamidine (1) would lead to a rapid hydrolysis of the prodrug to pentamidine diamidoxime (3) in the acidic stomach medium after oral application. Since the major portion of the gastrointestinal absorption, however, only takes place in the upper small intestine sections, an enteric formulation of this prodrug should be aimed for. In this manner, the prodrug would withstand the acidic environment in the stomach undamaged and could be absorbed later in the small intestine. The instability at pH 2.0 hence is to be classified as being unproblematic for the later use as a medicinal substance.

Solubility

N,N'-bis(succinyloxy)pentamidine (1) possesses very good solubility in the pH range from 7.4 to 9.0 (see table 1). The solubility in acidic medium (pH 2.0) could not be exactly characterized due to the hydrolysis in this medium described before. Experiments, however, showed here, too, that the solubility is in the mM range.

Table 1 shows the solubility of N,N'-bis(succinyloxy) pentamidine (1) in comparison to other developed pentamidine prodrugs. It becomes clear from this data that the dicarboxylic acid derivative (1) is the compound with the best solubility. Solely the pentamidine monoamidoxime is also soluble in the mM range at a neutral and slightly alkaline pH value. Yet, this compound still possesses a free amidine function which has a very disadvantageous effect on the oral bioavailability. These excellent solubility properties promote a later use as a medicinal substance since sufficient solubility is a basic prerequisite for sufficient oral absorption. In addition, the good solubility of the N,N'-bis(succinyloxy)pentamidine (1) also enables parenteral application forms such as injections or infusions.

Protein Binding

The analyses as to protein binding showed that this compound having a plasma protein binding of 97% disposes of a quite pronounced protein binding. The ascertained protein binding is in a range which is also described for other pentamidine prodrugs, and thus does not represent a disadvantage as compared to the other prodrugs.[9]

Prodrug Concept

The prodrug concept itself, on which the inventive compounds are based, was described in the patent applications WO2009095499 and DE102008007381.

The activation of the inventive prodrug proceeds via esterases and the mARC enzyme system and is hence independent of cytochrome P450 enzymes. The participation of P450 enzymes always involves the risk of interactions which are not described in our selected activation mechanism. Cytochrome P450 enzymes participate in metabolizing numerous medicinal substances. If several medicinal substances are taken which are metabolized via this enzyme system, a delay of the decomposition of the medicinal substances may ensue with clinically relevant side effects.

In Vitro Activation

Figure 4:
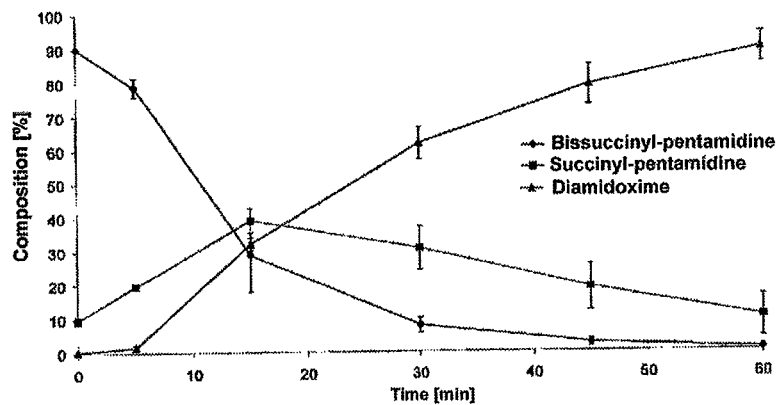
FIG. 4 is a activation of N,N'-bis(succinyloxy)pentamidine (1) by esterases.

The in vitro activation studies conducted the N,N'-bis (succinyloxy)pentamidine (1) activation takes place to good extent (table 2). The incubation with carboxyl esterases from porcine liver resulted in a rapid activation of the N,N'-bis (succinyloxy)pentamidine (1) (see FIG. 4). About 90% of the employed substrate was activated as early as after an incubation time of 60 min. This result shows that the first step of activating N,N'-bis(succinyloxy)pentamidine (1) to diamidoxime proceeds at an excellent speed.

The reduction to pentamidine could be detected in the incubations with subcellular enzyme preparations (table 2). In general, enzyme sources of porcine origin are more active than human ones, a fact which can be explained by the manner of obtaining the enzyme preparations. It should be taken into account that the processing of human organs is more problematic because of the very low initial amounts. In addition, porcine organs, as a rule, originate from healthy animals, whereas human tissue samples are in most cases taken from carcinoma patients after organ resection which constitutes an explanation for the comparably low conversion rates in using human enzyme preparations.

It can be stated in summary that the N,N'-bis(succinyloxy) pentamidine (1) is a suited prodrug of pentamidine. This study generally proves that the bioactivation of the prodrugs into the active compound takes place. The in vivo conversion rates can be expected to be clearly higher since the required enzymes are available in higher amounts.

Oral Bioavailability

Figure 5:
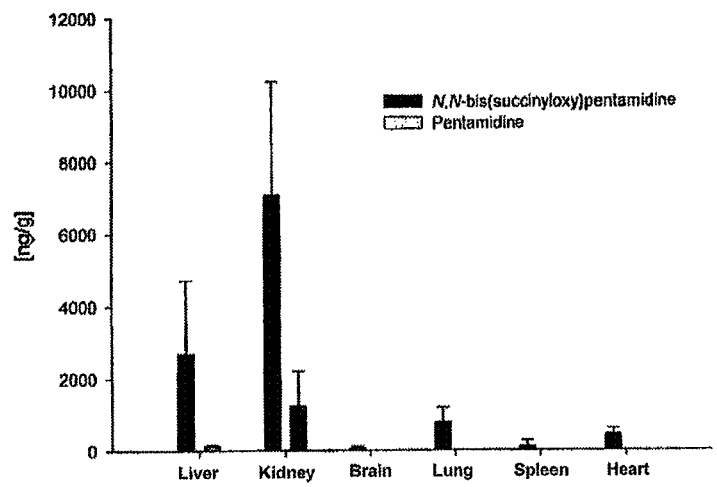
FIG. 5 is a content of pentamidine after p.o. application (50 mg/kg) of pentamidine and N,N'-bis(succinyloxy)pentamidine (1) in organs. Illustrated are the mean values of all tested rats.

The oral bioavailability of N,N'-bis(succinyloxy)pentamidine (1) could be demonstrated in the animal studies conducted. After orally administering the prodrug, pentamidine plasma levels could not be detected, a fact which can be explained by the known high pentamidine accumulation tendency in organs. The analysis of organ samples showed that N,N'-bis(succinyloxy)pentamidine (1) is orally bioavailable. After orally administering the prodrug, relevant concentrations could be identified in all examined organs (liver, kidney, lung, heart, brain and spleen). The highest concentrations were in this case detected in the kidney and liver (FIG. 5). The concentrations in spleen, heart, brain and lung were clearly lower. The relative oral bioavailability could be determined depending on the organ to be up to 98% (table 3).

In summary, the data proves the excellent suitability of the inventive prodrug principle for pentamidine. The pentamidine concentrations detected in the organs are in a range which enables the therapy of infections with trypanosomes ($IC_{50}$: 0.8-3.2 nM), leishmania ($IC_{50}$: 820-2590 nM), as well as plasmodia ($IC_{50}$: 35-129 nM).[13-16]

Summary

The newly developed prodrugs are orally bioavailable prodrugs of pentamidine. The prodrug principle used results in a considerable improvement of solubility which constitutes a very critical parameter of other pentamidine prodrugs. This improved solubility positively influences the pharmacokinetic behaviour of the substance since good solubility properties represent an important parameter in the absorption of medicinal substances, in particular in the gastrointestinal tract.

Except for the acidic pH range, compound 1 possesses good chemical stability. The marked hydrolysis in acidic medium is a condition for the prodrug to be administered as an enteric formulation when administered orally so as to preclude hydrolysis in the stomach.

The in vitro bioactivation assays could evidence a rapid and extensive activation of the prodrug into pentamidine. The activation proceeds independently of cytochrome P450 enzymes and hence does not involve the risk of interactions.

The good oral bioavailability could also be proven experimentally in the animal studies finally conducted. The pentamidine contents detected in the organs are in a range which enables efficiency with respect to infections by trypanosomes, leishmania and plasmodia.

In summary, the pentamidine dicarboxylic acid derivatives are excellent prodrugs which dispose of excellent physicochemical parameters and possess good oral bioavailability. Due to these properties, they are clearly superior to other pentamidine prodrugs. A use is possible both in cancer therapy and in the treatment of trypanosome, leishmania and pneumocystis carinii infections.

Material and Methods: Exemplary Embodiments

Syntheses

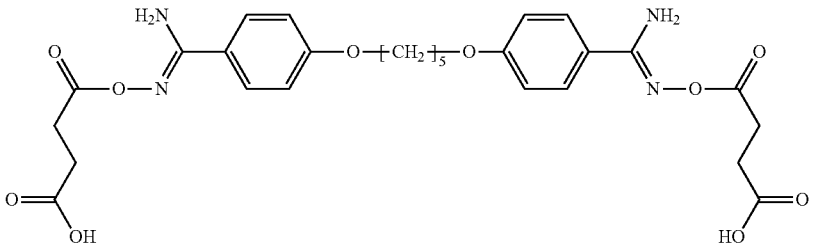

4,4'-Pentamethylendioxy-bis-[N-(carboxypropionyloxy)] benzamidine (N,N'-bis(succinyloxy)pentamidine) (1):

1 g pentamidine diamidoxime is dissolved in 250 ml acetone, and 540 mg succinic acid anhydride is added. The batch is stirred under reflux for 4 h. Subsequently, the solvent is removed under vacuum and the residue crystallized from toluene.

Yield: 68% Melting point: 141° C.

IR (KBr): v=3478, 3348, 2940, 2870, 1732, 1698, 1612, 1472, 1250 cm-1

1H NMR (DMSO-d6): δ/ppm (TMS)=1.59 (m, 2H, CH2), 1.79 (qn, 4H, 3J=6.7 Hz, CH2), 2.52 (t, 4H, 3J=6.6 Hz, CH2), 2.68 (t, 4H, 3J=6.6 Hz, CH2), 4.04 (t, 4H, 3J=6.5 Hz, O—CH2), 6.63 (s, 4H, NH2), 6.99 (mc, 4H, AA'BB', Ar—H), 7.65 (mc, 4H, AA'BB', Ar—H), 12.18 (brs, 2H, COOH)

13C-NMR (DMSO-d6): δ/ppm (TMS)=22.1 (CH2), 27.9 (CH2), 28.3 (CH2), 28.8 (CH2), 67.5 (O—CH2), 113.9 (ArCH), 123.5 (ArC), 128.1 (ArCH), 156.2 (ArC), 160.3 (C-NH2), 170.2 (COOR), 173.5 (COOH)

MS (ESI) m/z: 573 [M+H]+, 555 [M−H2O+H]+, 473 [M−C4H4O3+H]+, 455 [M−C4H4O3−H2O+H]+, 373 [DAO+H]+, 178

Elementary analysis C27H32N4O10 (molecular mass: 572.56): Calculated: C 56.64, H 5.63, N 9.79. Found: C 56.85, H 6.01, N 9.60.

Syntheses

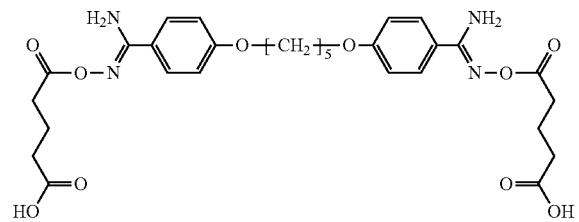

4,4'-Pentamethylendioxy-bis-[N-(carboxybutionyloxy)] benzamidine (N,N'-bis(glutaryloxy)pentamidine)(2):

1 g pentamidine diamidoxime is dissolved in 250 ml acetone, and 616 mg glutaric acid anhydride is added. The batch is stirred under reflux for 4 h. Subsequently, the solvent is removed under vacuum and the residue crystallized from toluene.

Yield: 80% Melting point: 155° C.

IR (KBr): ν=3495, 3350, 2950, 2874, 1747, 1700, 1619, 1520, 14225, 1258 cm-1

1H NMR (DMSO-d6): δ/ppm (TMS)=1.59 (m, 2H, CH2), 1.81 (m, 8H, CH2), 2.29 (t, 4H, 3J=7.4 Hz, CH2), 2.49 (t, 4H, 3J=7.1 Hz, CH2), 4.04 (t, 4H, 3J=6.4 Hz, O—CH2), 6.63 (s, 4H, NH2), 6.98 (m, 4H, AA'BB', Ar—H), 7.65 (m, 4H, AA'BB', Ar—H), 12.05 (s, 2H, COOH)

13C-NMR (DMSO-d6): δ/ppm (TMS)=19.9 (CH2), 22.1 (CH2), 28.3 (CH2), 31.6 (CH2), 32.8 (CH2), 67.5 (O—CH2), 114.1 (ArCH), 123.5 (ArC), 128.1 (ArCH), 156.1 (ArC), 160.3 (C-NH2), 170.6 (COOR), 173.9 (COOH)

MS (ESI) m/z: 601 [M+H]+, 169

Elementary analysis C29H36N4O10 (molecular mass: 600.62): Calculated: C 57.99, H 6.04, N 9.33. Found: C 58.05, H 6.24, N 9.72.

Alternative synthesis of N,N'-bis(succinyloxy)pentamidine (1) and N,N'-bis(glutaryloxy)pentamidine (2)

The preparing of the prodrugs (1, 2) ensued from pentamidine diamidoxime (3) and the respective acid anhydride (succinic acid respectively glutaric acid anhydride).

For producing the prodrug (1), the pentamidine diamidoxime (3) was dissolved in ethanol, and a tenfold excess of succinic acid anhydride, dissolved in dichloromethane, was added to the solution by drops. The mixture was heated for four hours under reflux, allowed to cool down to room temperature, the formed precipitate was filtered off and subsequently rinsed several times with dichloromethane. Compound (1) could be prepared analytically pure at a very good yield. For producing the prodrug (2), the starting compound was heated for 4 h under reflux in dried acetone while adding glutaric acid anhydride (see FIG. 1). By subsequently boiling up in toluene and directly filtering off, substance 2 could be separated and prepared analytically pure.

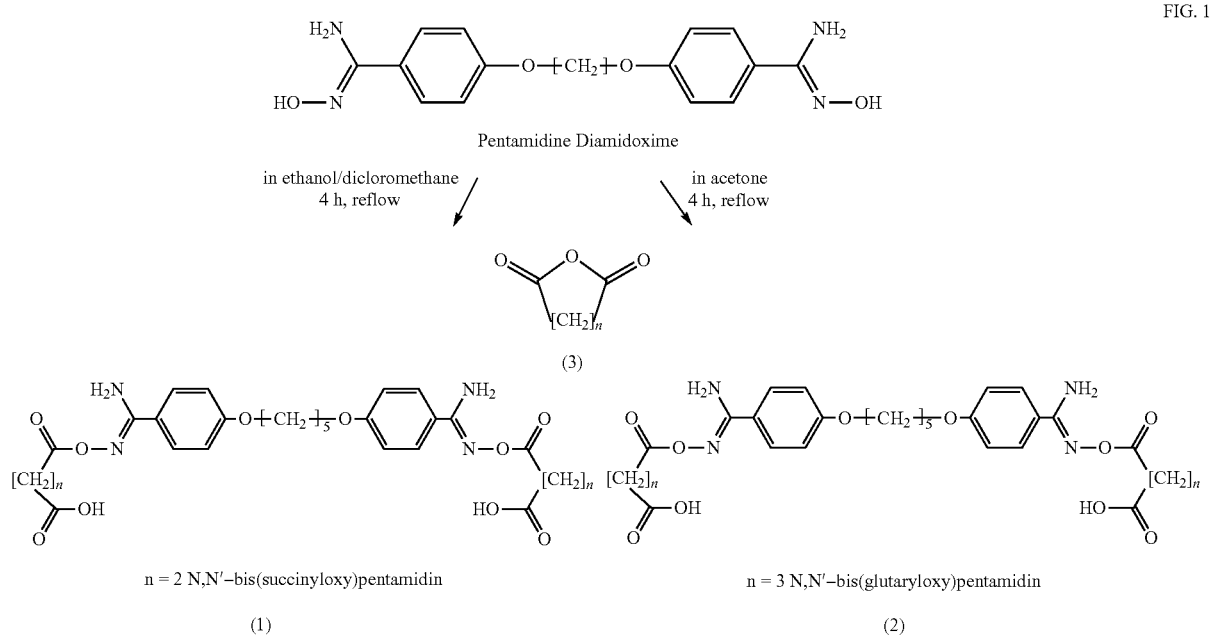

FIG. 1

Characterization of the Pentamidine Prodrugs

Stability Analyses of the N,N'-bis(succinyloxy)pentatnidine (1)

For the stability analyses, a 0.1 mM solution of N,N'-bis(succinyloxy)pentamidine (1) was prepared in a 50 mM potassium phosphate buffer/DMSO (90/10, vol/vol). The analysis took place at pH values of 2.0, 7.4 and 9.0. One sample was taken and immediately analyzed by HPLC every 15 min over a period of 150 min.

Further analyses were conducted with human and murine plasma. 900 μl of the plasma was mixed with 100 μl of a 2 mM solution of N,N'-bis(succinyloxy)pentamidine (1). The final concentration of N,N'-bis(succinyloxy)pentamidine (1) was thus 0.2 mM. The samples were incubated at 37° C. in a shaking water bath and samples were taken after 0, 15, 30, 45, 60, 75, 90, 105 and 120 min. For this purpose, 100 μl was drawn in each case and mixed with 100 μl acetonitrile. The samples were shaken, centrifuged for 5 min and the supernatant was measured by HPLC.

In addition, incubations with carboxyl esterase from pig liver were conducted. For this purpose, N,N'-bis(succinyloxy)pentamidine (1) was incubated in a concentration of 0.1 mM with 1 U esterase in 250 μl 50 mM phosphate buffer, pH 7.4, at 37° C. over a period of 60 min. At intervals of 15 min each, the samples were analyzed via HPLC.

The stability analyses were evaluated by means of the following HPLC method:

| | |
|---|---|
| HPLC system | Waters Alliance ™ HPLC system with Waters e2695 XC Separations Modul, Waters 2998 Photodiode Array Detector and Empower ™ 2 imaging and evaluation software |
| Stationary phase | Synergi Max-RP 80A (Phenomenex, 250 × 4.6 mm; 4 μm) with a Phenomenex C18 (4 × 3.0 mm) precolumn |

-continued

| Mobile phase | A | 45% | 20 mM phosphate buffer pH 7.0 |
| --- | --- | --- | --- |
| | B | 55% | Methanol |
| Detection | 210-400 nm (260 nm) | | |
| Flow rate | 1.0 ml/min | | |
| Run time | 12 min | | |
| Column temperature | 25° C. | | |
| Injection volume | 10 μl | | |
| Retention times | N,N'-bis(succinyloxy)pentamidine (1): 3.2 ± 0.1 min | | |
| | succinyloxypentamidine: 4.8 ± 0.1 min | | |
| | pentamidine diamidoxime (3): 8.1 ± 0.2 min | | |

Solubility of N,N'-bis(succinyloxy)pentamidine (1)

An amount of the compound which is insoluble in 100 μl was suspended in 50 mM of a phosphate buffer (pH 7.4, respectively pH 9.0) and shaken for 20 min. Subsequently, the undissolved part was removed by centrifugation (12,000 rpm) and the samples were immediately measured by HPLC. The evaluation of the solubility ensued via a calibration of N,N'-bis(succinyloxy)pentamidine (1) in DMSO. The compound dissolves well (7.5 mM) at a physiological pH value of 7.4. The solubility is further improved when the pH value is increased (see table 1).

Various other pentamidine prodrugs were examined by comparison so as to be able to better judge the solubility as compared to previously described derivatives.

Solubilities were determined analogously to the method described for compound 1.

TABLE 1

Solubility of the N,N'-bis(succinyloxy)pentamidine (1) and other pentamidine prodrugs at various pH values

| Pentamidine prodrug | Solubility [μM] | | |
| --- | --- | --- | --- |
| | pH 2.0 | pH 7.4 | pH 9.0 |
| N,N'-bis(succinyloxy)pentamidine (1) | hydrolysis | 7500 ± 340 | 10780 ± 70 |
| Pentamidine monoamidoxime | 22285 ± 1244 | 1370 ± 291 | 1257 ± 40 |
| Pentamidine diamidoxime (3) | 4211 ± 231 | 12 ± 1 | 4 ± 1 |
| N,N'-bis(acetoxy)pentamidine | 14 ± 8 | 2 ± 1 | 3 ± 2 |
| N,N'-bis(methoxy)pentamidine | 1304 ± 28 | 8 ± 1 | 10 ± 2 |
| N,N'-bis(dihydroxy)pentamidine | >35000 | 95 ± 8 | 21 ± 3 |
| N,N'-bis(valoxy)pentamidine | >35000 | 157 ± 19 | 84 ± 18 |

Determination of the Protein Binding of the N,N'-bis(succinyloxy)-pentamidine (1)

The plasma protein binding was determined at three different concentrations (10, 20 and 50 μM). A 4% albumin solution was used as the protein solutions. 50 μl of a 10 times concentrated substance solution were in each case pipetted to 450 μl of the protein solution. Incubation ensued over 15 min in a shaking water bath at 37° C. Subsequently, the samples were transferred into ultrafiltration units (Vivaspin 500, 10 kDa cut off) and centrifuged for 15 min at 10,000 RPM. The filtrate was analyzed by HPLC. Additionally, a control which was not mixed with protein nor centrifuged was carried out for each concentration. A further control without protein addition which, however, was centrifuged by the filtration unit showed that the prodrugs had not been retained by the diaphragm and served to validate the methodology.

The analysis of the sample identified a compound 1 protein binding of 97.1±1.2%.

Analysis of the N,N'-bis(succinyloxy)pentamidine (1) bioactivation

Ascertaining Prodrug Activation using Various Subcellular Enzyme Systems

The activation of the prodrug was determined in vitro by means of subcellular enzyme preparations. 9000×g of supernatants, microsomes and mitochondria of human and porcine liver and kidney tissues were used as the enzyme preparations. The incubation batches were composed of 500 mM prodrug, 1 mM NADH, 1 U esterase and 0.3 mg enzyme preparation dissolved in 150 μl 100 mM phosphate buffer, pH 6.3. The incubation took place over 20 min in a shaking water bath at 37° C. The incubation was terminated by adding 150 μl of acetonitrile. The samples were subsequently shaken for 10 min and the precipitated protein was removed by centrifuging at 10,000 RPM for 15 min. The supernatant was measured by means of HPLC. The identified conversion rates are indicated in table 2.

TABLE 2

Activation of the N,N'-bis(succinyloxy)pentamidine (1) into the active form using subcellular enzyme preparations, HL = human liver, HN = human kidney, SL = pig liver, SN = pig kidney, 9000 g = 9000 g supernatant, MS = microsomes, Mt = mitochondria

| Enzyme source | Pentamidine [nmol * min$^{-1}$ * mg$^{-1}$] |
| --- | --- |
| HL 9000 g | 0.04 ± 0.01 |
| HL Ms | 0.02 ± 0.02 |
| HL Mt | 0.56 ± 0.43 |
| HN Mt | 0.08 ± 0.02 |
| SL 9000 g | 0.00 ± 0.00 |
| SN 9000 g | 0.49 ± 0.03 |
| SL Ms | 0.69 ± 0.13 |
| SN Ms | 2.25 ± 0.58 |
| SL Mt | 1.44 ± 0.22 |
| SN Mt | 0.41 ± 0.09 |

In addition, incubations were performed using 1 U carboxyl esterase from pig liver. For this purpose, the compound was incubated over 60 min in a concentration of 500 μM with 1 U esterase in 250 μl 50 mM phosphate buffer, pH 7.4. The incubations were terminated by adding 250 μl of acetonitrile. The incubations using carboxyl esterases from pig liver led to a rapid activation of the N,N'-bis(succinyloxy)pentamidine (1) (see FIG. 4). About 90% of the substrate employed was activated already after an incubation time of 60 min. This result shows that the first step of the N,N'-bis(succinyloxy)pentamidine (1) activation into diamidoxime proceeds at high speed.

HPLC Method for Determining the Pentamidine

| HPLC system | Waters Alliance HPLC system with Waters e2695 XC Separations Modul, Waters 2998 Photodiode Array Detector and Empower 2 Software |
| --- | --- |
| Column | LiChroCart LiChrospher 60 RP-select B, 125 × 4 mm, 5 μm |
| Flow | 1 ml/min |
| Flow agent | 52% 20 mM tetramethyl ammonium chloride/ 10 mM octyl sulfonate pH 3.0 48% MeOH |
| Run time | 15 min |
| Detection | 260 nm |
| Injection volume | 20 μl |
| Retention time | pentamidine 10.7 ± 0.4 min |

Oral bioavailability (Animal Study)

Pentamidine was administered intravenously to 10 rats in a concentration of 10 mg/kg. N, N'-bis(succinyloxy)pentamidine (1) was administered to 10 rats each in a concentration of 50 mg/kg as a suspension with Arabic gum (10% m/V) per gavage. 100 mM of potassium phosphate buffer of pH 9.0 was used in preparing the suspension so as to prevent premature cleavage of the succinyl ester in the acidic environment of the stomach. In addition, 3 rats were given pentamidine at a dosage of 50 mg/kg per gavage in order to determine the oral bioavailability of the active form itself.

After the intravenous administration, plasma samples were taken after 5, 10, 40, 75, 150 and 300 min, respectively 20, 40, 60, 90, 120, 240 and 360 min after oral administration. For this purpose, 300 µl of whole blood was drawn using an insulin syringe and transferred into EDTA-coated CB 300 microvettes (Sarstedt, Nümbrecht). After each withdrawal, the sample was rinsed with 100 µl of 0.9% saline solution respectively with heparin solution (250 I.E./ml) at an interval of 60 min. The blood sample was briefly shaken and placed on ice until centrifugation (4° C.; 14,000 RPM; 10 min). The samples were stored further at −80° C.

Slaughter ensued by guillotine decapitation 6 hours after the drug administration. The organs were subsequently removed. All organs were cleaned and frozen in 2-methylbutane cooled in dry ice. Liver, kidney, lung, spleen, heart and brain were removed.

Sample Preparation

1. Plasma Samples:

The plasma samples were defrosted at room temperature. 65 µl of acetonitrile was prepared in each case and 65 µl of the plasma samples added by pipetting. The samples were subsequently shaken for 45 min. The samples were centrifuged at 10,000 RPM for 15 min and the supernatant was transferred into HPLC vials. 35 µl was used in each case for the HPCL determinations.

Calibrations and analyses for recovering the pentamidine were performed in a phosphate buffer of pH 7.4, murine plasma respectively, so as to quantitatively evaluate the plasma samples.

2. Organ Samples

The organs were defrosted at room temperature and weighed. Depending on the respective organ, differing amounts of the tissues were prepared. About 1000 mg were used in case of the liver samples; about 500 mg in case of all of the other organs. The organs were minced by means of a potter. For this purpose, each of the weighed tissues were minced with 1 ml aqua bidest for 5 min. The potter vessel was subsequently rinsed in each case with 1 ml of aqua bidest. The samples were transferred into reaction vessels and the same volume of acetonitrile was added in order to precipitate proteins. The samples were shaken for 45 min and subsequently centrifuged at 12,000 RPM for 15 min. The supernatant was transferred into glass bottles and concentrated under compressed air. The residue was washed with 500 µl of acetonitrile, re-centrifuged, and the supernatant added to the remaining samples. The residue was discarded. After concentrating under compressed air, the samples were freeze-dried overnight.

The solubilizing of the samples ensued with 400 µl of a mixture of methanol/aqua bidest (50/50). The samples were shaken at room temperature for 1.5 hours and the residue subsequently removed by centrifugation (15,000 RPM, 15 min). The concentration of pentamidine was determined from the supernatant by means of HPLC.

Results of the Animal Study

The analysis of the plasma samples after intravenous administration of the pentamidine rendered detectable plasma levels over a period of 300 min. After oral administration of the prodrug, plasma concentrations of pentamidine could not be detected. This phenomenon is known for pentamidine derivatives since they tend to accumulate in the tissues to a very pronounced extent. Consequently, a direct calculation of the bioavailability across plasma concentrations could not be performed. The pentamidine concentrations in the examined organs were therefore used for determining the relative bioavailability.

Evaluation of the Organ Samples and Bioavailability

The analysis of the processed samples yielded detectable contents of pentamidine in all of the examined organs—with the highest concentrations in the liver and kidney. The concentrations in lung, spleen and heart are clearly lower. The lowest concentrations of pentamidine were detected in the brains. The results are summarized in FIG. 5.

The oral bioavailability of a compound is in general determined via the plasma concentrations after oral and intravenous application of the compound. Due to the high protein binding of pentamidine and its pronounced tendency to accumulate in tissues, however, plasma concentrations could not be determined after oral application of the pentamidine prodrug. Rather the detected contents than the plasma concentrations in the examined organs (liver, kidney, lung, spleen, heart, brain) are therefore used for calculating the relative bioavailability. Relative bioavailability of the pentamidine prodrug could be calculated via the comparison after intravenous application of the active form and oral application of the prodrug. The different dosages were taken into account in the calculation. The relative bioavailabilities are illustrated in table 3. The highest bioavailability of 98% was identified in the liver. The bioavailability in the other tissues is clearly reduced. The high bioavailability in the liver may be explained by the bioactivation of the prodrug. Same takes place preponderantly in the liver which explains the comparably high concentrations in this organ. The concentration in the brain is very low which is indicative of the prodrug passing the blood-brain-barrier only to a very low extent.

TABLE 3

Relative bioavailability of pentamidine derivatives
Pentamidine concentration [µg/g organ] and relative bioavailability [%]

|  | Pentamidine i.v. (10 mg/kg) | Pentamidine p.o. (50 mg/kg) | rBV [%] | N,N'-bis(succinyloxy)-pentamidine p.o. (50 mg/kg) | rBV [%] |
|---|---|---|---|---|---|
| Liver | 0.53 ± 0.33 | 0.12 ± 0.03 | 4.5 ± 1.1 | 2.68 ± 2.02 | 97.8 ± 73.7 |
| Kidney | 22.03 ± 4.16 | 1.24 ± 0.96 | 1.1 ± 0.9 | 7.07 ± 3.15 | 6.2 ± 2.8 |
| Lung | 3.03 ± 1.04 | n.d. | — | 0.76 ± 0.42 | 4.9 ± 2.7 |
| Spleen | 1.97 ± 1.00 | n.d. | — | 0.10 ± 0.16 | 1.0 ± 1.6 |
| Heart | 2.41 ± 0.74 | n.d. | — | 0.43 ± 0.16 | 3.5 ± 1.3 |
| Brain | 0.22 ± 0.12 | n.d. | — | 0.06 ± 0.05 | 5.3 ± 4.4 | rBV = relative bioavailability

HPLC Analytics

The following HPLC analytics was used for analyzing the organ and plasma samples after intravenous application of pentamidine:

| | |
|---|---|
| HPLC system | Waters Autosampler 717plus, Waters 600 Controller, Waters 600 Pump, Waters 2487 Dual λ Absorbance Detector and EZChrom Elite Client/Server imaging and evaluation software (Version 2.8.3) |
| Stationary phase | Superspher 60 RP-select B (250 × 3 mm); precolumn: Merck LiChrospher 60 RP-select B (4 × 4 mm, 5 μm) |
| Mobile phase | 40% methanol<br>60% TFA 0.1% pH 2.5 |
| Detection | $\lambda_{Ex}$ = 275 nm; $\lambda_{Em}$ = 340 nm |
| Flow rate | 0.32 ml/min |
| Run time | 35 min |
| Injection volume | 35 μl |
| Retention time | pentamidine: 22.4 ± 1.2 min |

The following HPLC analytics was used for analyzing the organ and plasma samples after oral application of the pentamidine prodrug:

| | |
|---|---|
| HPLC-System | Waters Alliance ™ HPLC-System with Waters e2695 XC Separations Modul, Waters 2998 Photodiode Array Detector and Empower ™ 2 imaging and evaluation software |
| Stationary phase | Superspher 60 RP-select B (250 × 3 mm); precolumn: Merck LiChrospher 60 RP-select B (4 × 4 mm, 5 μm) |
| Mobile phase | 40% methanol<br>60% TFA 0.1% pH 2.5 |
| Detection | 210-300 nm (260 nm) |
| Flow rate | 0.32 ml/min |
| Run time | 35 min |
| Injection volume | 35 μl |
| Retention time | diamidoxime 20.0 ± 0.3 min<br>monoamidoxime: 22.5 ± 0.4 min<br>pentamidine: 24.7 ± 0.5 min |

Storage Stability:

Samples were stored at room temperature and 70° C. over a defined period and examined for analyzing the prodrug (1) storage stability. The storage period was 6 months for the room temperature samples, 7 days for the 70° C. samples. The prodrug (1) content was determined by means of HPLC. For this purpose, the samples were dissolved in a mixture of equal parts of methanol and phosphate buffer (20 mM, pH 7.4) and immediately measured. The HPLC method corresponds to the method described under "Characterization of the prodrugs".

Figure 6:
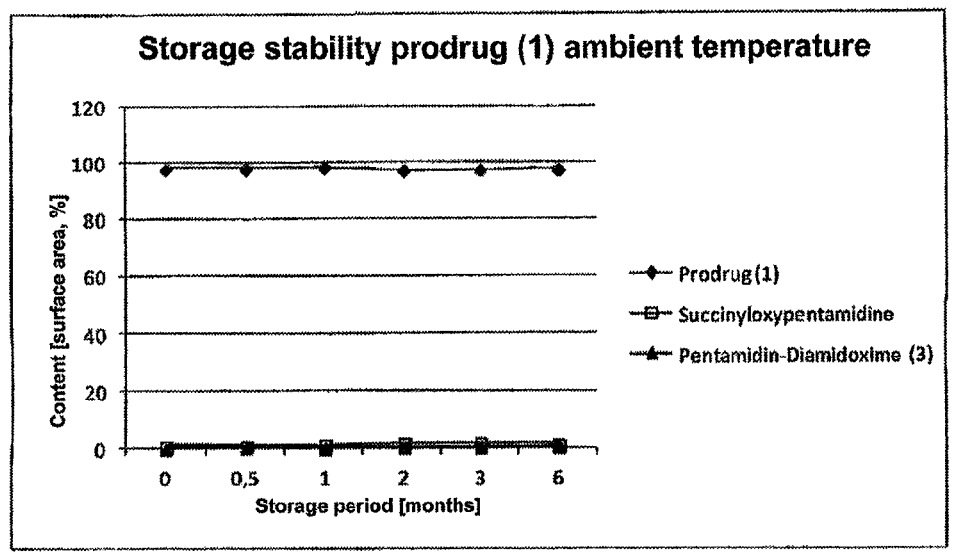
FIGS. 6 and 7 are the results of the storage stability illustrated in tables 4 and 5 are shown in graphical form in FIGS. 6 and 7.
Figure 7:
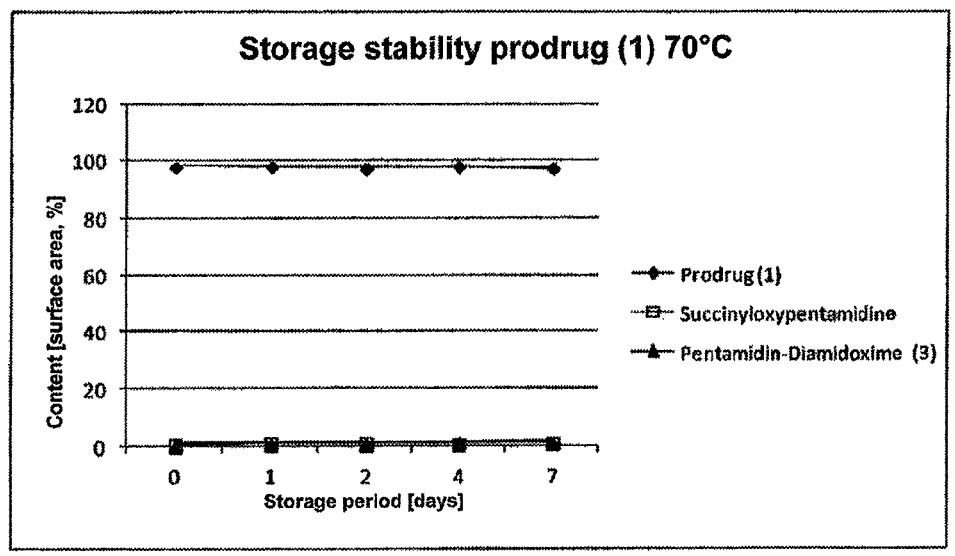

It could be shown that prodrug (1) exhibited a very high stability within the examined period both at room temperature and 70° C. (see tables 3, 4, and FIGS. 6, 7). Apart from prodrug (1), succinyloxypentamidine and pentamidine diamidoxime (3) were found.

TABLE 4

Storage stability of N,N'-bis(succinyloxy)pentamidine (1) at room temperature

| | content [HPLC, area %] | | |
|---|---|---|---|
| time [months] | prodrug (1) | succinyloxypentamidine | pentamidine diamidoxime(3) |
| 0 months | 98.4 ± 0.01% | 1.0 ± 0.02% | 0.4 ± 0.01% |
| 0.5 months | 98.4 ± 0.03% | 1.0 ± 0.03% | 0.5 ± 0.01% |
| 1 month | 98.6 ± 0.14% | 1.2 ± 0.16% | 0.2 ± 0.02% |
| 2 months | 97.5 ± 0.02% | 1.8 ± 0.02% | 0.6 ± 0.16% |
| 3 months | 97.5 ± 0.04% | 1.8 ± 0.04% | 0.6 ± 0.01% |

TABLE 4-continued

Storage stability of N,N'-bis(succinyloxy)pentamidine (1) at room temperature

| | content [HPLC, area %] | | |
|---|---|---|---|
| time [months] | prodrug (1) | succinyloxypentamidine | pentamidine diamidoxime(3) |
| 6 months | 97.8 ± 0.19% | 1.5 ± 0.19% | 0.5 ± 0.01% |

TABLE 5

Storage stability of N,N'-bis(succinyloxy)pentamidine (1) at 70° C.

| | content [HPLC, area %] | | |
|---|---|---|---|
| time [days] | prodrug (1) | succinyloxypentamidin | Pentamidine Diamidoxime (3) |
| 0 days | 98.4 ± 0.01% | 1.0 ± 0.02% | 0.4 ± 0.01% |
| 1 day | 98.0 ± 0.02% | 1.1 ± 0.03% | 0.9 ± 0.01% |
| 2 days | 97.6 ± 0.19% | 1.3 ± 0.20% | 1.0 ± 0.01% |
| 4 days | 97.9 ± 0.01% | 0.9 ± 0.01% | 1.1 ± 0.01% |
| 7 days | 97.4 ± 0.39% | 1.1 ± 0.26% | 1.5 ± 0.13% |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

REFERENCE LIST

1. Chow, T. Y.; Alaoui-Jamali, M. A.; Yeh, C.; Yuen, L.; Griller, D. The DNA double-stranded break repair protein endo-exonuclease as a therapeutic target for cancer. Mol Cancer Ther 2004, 3, 911-9.

2. Pharma, O. Inhibitors of Endo-Exonuclease activity for treating cancer. 2001.

3. Pharma, O. Pentamidine Combinations for Treating Cancer. 2010.

4. Clement, B. Reduction of N-hydroxylated compounds: amidoximes (N-hydroxyamidines) as pro-drugs of amidines. Drug Metab Rev 2002, 34, 565-79.

5. Clement, B.; Schmitt, S.; Zimmermann, M. Enzymatic reduction of benzamidoxime to benzamidine. Arch Pharm (Weinheim) 1988, 321, 955-6.

6. Clement, B.; Immel, M.; Terlinden, R.; Wingen, F. J. Reduction of amidoxime derivatives to pentamidine in vivo. Arch Pharm (Weinheim) 1992, 325, 61-2.

7. Havemeyer, A.; Bittner, F.; Wollers, S.; Mendel, R.; Kunze, T.; Clement, B. Identification of the missing component in the mitochondrial benzamidoxime prodrug-converting system as a novel molybdenum enzyme. J Biol Chem 2006, 281, 34796-802.

8. Gruenewald, S.; Wahl, B.; Bittner, F.; Hungeling, H.; Kanzow, S.; Kotthaus, J.; Schwering, U.; Mendel, R. R.; Clement, B. The fourth molybdenum containing enzyme mARC: cloning and involvement in the activation of N-hydroxylated prodrugs. J Med Chem 2008, 51, 8173-7.

9. Clement, B.; Burenheide, A.; Rieckert, W.; Schwarz, J. Diacetyldiamidoximeester of pentamidine, a prodrug for treatment of protozoal diseases: synthesis, in vitro and in vivo biotransformation. ChemMedChem 2006, 1, 1260-7.

10. Clement, B. R., C. Improvement of the bioavailability of active substances having an amidine function in medicaments. 2008.

11. Clement, B. R., C.; Hungeling, H. Use of amidoxime carboxylic acid esters and N-hydroxyguanidine carboxylic acid esters for producing prodrugs. 2009.

12. Reeh, C.; Wundt, J.; Clement, B. N,N'-dihydroxyamidines: a new prodrug principle to improve the oral bioavailability of amidines. J Med Chem 2007, 50, 6730-4.

13. Arafa, R. K.; Brun, R.; Wenzler, T.; Tanious, F. A.; Wilson, W. D.; Stephens, C. E.; Boykin, D. W. Synthesis, DNA affinity, and antiprotozoal activity of fused ring dicationic compounds and their prodrugs. J Med Chem 2005, 48, 5480-8.

14. Brendle, J. J.; Outlaw, A.; Kumar, A.; Boykin, D. W.; Patrick, D. A.; Tidwell, R. R.; Werbovetz, K. A. Antileishmanial activities of several classes of aromatic dications. Antimicrob Agents Chemother 2002, 46, 797-807.

15. Donkor, I. O.; Huang, T. L.; Tao, B.; Rattendi, D.; Lane, S.; Vargas, M.; Goldberg, B.; Bacchi, C. Trypanocidal activity of conformationally restricted pentamidine congeners. J Med Chem 2003, 46, 1041-8.

16. Ismail, M. A.; Brun, R.; Wenzler, T.; Tanious, F. A.; Wilson, W. D.; Boykin, D. W. Dicationic biphenyl benzimidazole derivatives as antiprotozoal agents. Bioorg Med Chem 2004, 12, 5405-13.

We claim:

1. A compound of formula:

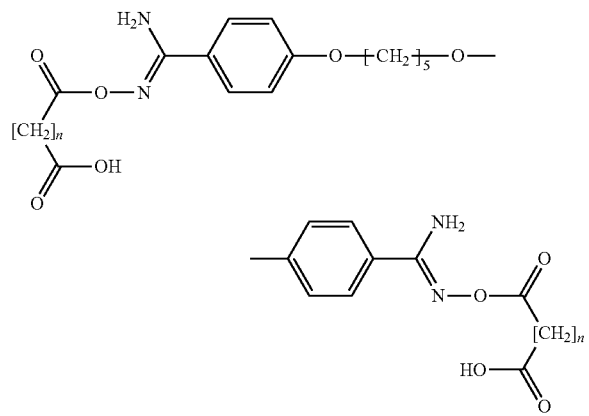

wherein n is an integer selected from 1 to 10,
or a pharmaceutically acceptable derivative thereof.

2. The compound according to claim 1, wherein n is 2.

3. The compound according to claim 1, wherein n is 3.

4. A salt, a solvate or a solvate of the salt of the compound according to claim 1.

5. A drug comprising the compound according to claim 1, and one or more of inert, non-toxic, and pharmaceutically suitable excipients.

6. The drug according to claim 5, wherein n is 2.

7. The drug according to claim 5, wherein n is 3.

8. The drug according to claim 5, further comprising one or more additional active agent(s).

9. The drug according to claim 5, being for oral or parenteral administration.

10. The drug according to claim 5, being an enteric formulation.

11. A method for preparing a compound of formula (C):

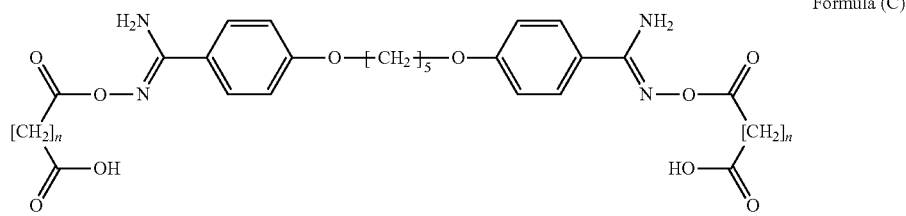

comprising reacting amidoxime of formula (A):

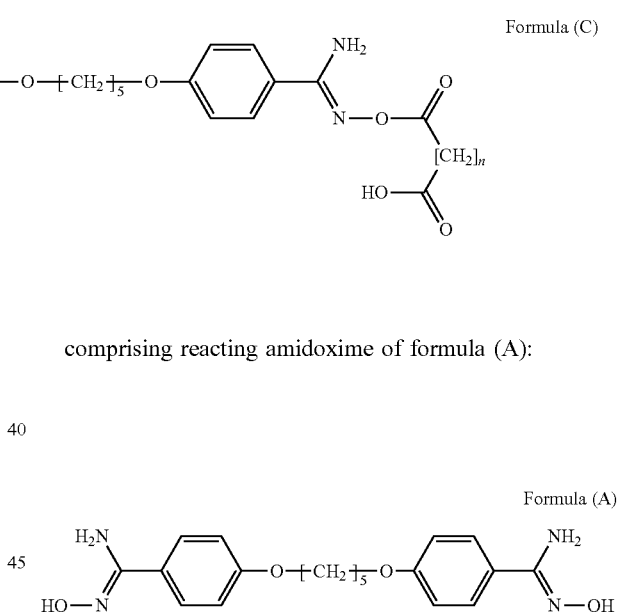

with a dicarboxylic acid anhydride of formula (B):

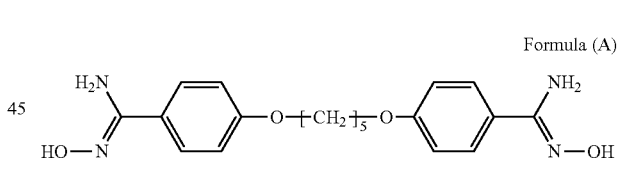

to obtain the compound of formula (C),
wherein n is an integer selected from 1 to 10.

* * * * *